US009241952B2

(12) United States Patent
Gorgani et al.

(10) Patent No.: US 9,241,952 B2
(45) Date of Patent: Jan. 26, 2016

(54) METHOD OF TREATING TYPE II DIABETES, HYPERGLYCEMIA OR HYPOGLYCEMIA BY ADMINISTERING A SYNERGISTIC COMBINATION OF A SULPHONYLUREA AND INULIN

(75) Inventors: Nick Naser Gorgani, Waverton (AU); Mahnoosh Afkham, Waverton (AU)

(73) Assignee: OZSTAR THERAPEUTICS PTY LTD, Waverton, New South (AU)

( * ) Notice: Subject to any disclaimer, the term of this patent is extended or adjusted under 35 U.S.C. 154(b) by 67 days.

(21) Appl. No.: 13/699,371

(22) PCT Filed: May 24, 2011

(86) PCT No.: PCT/AU2011/000622
§ 371 (c)(1),
(2), (4) Date: Nov. 21, 2012

(87) PCT Pub. No.: WO2011/146981
PCT Pub. Date: Dec. 1, 2011

(65) Prior Publication Data
US 2013/0072454 A1    Mar. 21, 2013

(30) Foreign Application Priority Data
May 24, 2010    (AU) .................................. 2010902262

(51) Int. Cl.
*A61K 31/733*    (2006.01)
*A61K 31/64*    (2006.01)
*A61K 36/28*    (2006.01)

(52) U.S. Cl.
CPC .............. *A61K 31/733* (2013.01); *A61K 31/64* (2013.01); *A61K 36/28* (2013.01)

(58) Field of Classification Search
None
See application file for complete search history.

(56) References Cited

U.S. PATENT DOCUMENTS

| | | | |
|---|---|---|---|
| 4,505,921 A | 3/1985 | Beregi et al. | |
| 5,550,113 A | 8/1996 | Mann | |
| 5,859,037 A | 1/1999 | Whitcomb | |
| 5,972,973 A | 10/1999 | Whitcomb | |
| 6,011,049 A | 1/2000 | Whitcomb | |
| 2003/0077335 A1* | 4/2003 | Richardson et al. | 424/682 |
| 2003/0130205 A1 | 7/2003 | Christian | |
| 2009/0214511 A1 | 8/2009 | Tran et al. | |
| 2009/0214718 A1 | 8/2009 | Leusner | |
| 2010/0303931 A1 | 12/2010 | Feltin et al. | |
| 2011/0217368 A1 | 9/2011 | Prakash et al. | |
| 2011/0318321 A1 | 12/2011 | Selva et al. | |
| 2012/0045486 A1 | 2/2012 | Bravo Cordero et al. | |
| 2013/0072454 A1 | 3/2013 | Gorgani et al. | |

FOREIGN PATENT DOCUMENTS

| | | |
|---|---|---|
| CN | 1491639 A | 4/2004 |
| EP | 1 935 424 A1 | 6/2008 |
| GB | 2304046 A | 3/1997 |
| WO | 2006138705 A1 | 12/2006 |
| WO | 2008138805 A1 | 11/2008 |
| WO | 2010/084038 A1 | 7/2010 |
| WO | 2010122357 A2 | 10/2010 |
| WO | 2010/124387 A1 | 11/2010 |
| WO | 2011146981 A1 | 12/2011 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002.*
Karunakara, S., Hammersley, M. S., Morris, R. J., Turner, R. C., & Holman, R. R. (1997). The Fasting Hyperglycaemia Study: III. Randomized controlled trial of sulfonylurea therapy in subjects with increased but not diabetic fasting plasma glucose. Metabolism, 46, 56-60.*
Moshfegh, A. J., Friday, J. E., Goldman, J. P., & Ahuja, J. K. C. (1999). Presence of inulin and oligofructose in the diets of Americans. The Journal of nutrition, 129(7), 1407S-1411s.*
Rendell, M. (2004). The role of sulphonylureas in the management of type 2 diabetes mellitus. Drugs, 64(12), 1339-1358.*
Hannan, J. M. A., Marenah, L., Ali, L., Rokeya, B., Flatt, P. R., & Abdel-Wahab, Y. H. (2007). Insulin secretory actions of extracts of Asparagus racemosus root in perfused pancreas, isolated islets and clonal pancreatic β-cells. Journal of endocrinology, 192(1), 159-168.*
Alles, M. S., de Roos, N. M., Bakx, J. C., van de Lisdonk, E., Zock, P. L., & Hautvast, J. G. (1999). Consumption of fructooligosaccharides does not favorably affect blood glucose and serum lipid concentrations in patients with type 2 diabetes. The American journal of clinical nutrition, 69(1), 64-69.*
Official Action related to corresponding Chinese Patent Application No. 201180036057.1, dated Jan. 24, 2014.
European Supplemental Search Report from corresponding European Patent Application No. 11785908.2 dated Oct. 15, 2013.
Written Opinion related to corresponding PCT/AU2012/001442 dated Jan. 31, 2013.
Further Written Opinion related to corresponding PCT/AU2012/001442 dated Oct. 25, 2013.
Kim G. Jackson et al. "The effect of the daily intake of insulin on fasting lipid, insulin and glucose concentrations in middle-aged men and women" British Journal of Nutrition, vol. 82, No. 1, [Jul. 1999], pp. 23-30.
International Search Report, dated Aug. 22, 2011, issued in corresponding PCT/AU2011/000622.

* cited by examiner

*Primary Examiner* — Eric Olson
*Assistant Examiner* — Dale R Miller
(74) *Attorney, Agent, or Firm* — Millen White Zelano and Branigan, PC; John Sopp; Anthony Zelano

(57) ABSTRACT

The present invention is concerned with synergistic compositions effective in the treatment of diabetes. In particular, the present invention is concerned with synergistic compositions comprising inulin, or a suitable source thereof, and Sulphonylureas used in the treatment of type-2 Diabetes Mellitus (T2DM) and hyperglyacemia.

10 Claims, 6 Drawing Sheets

METHOD OF TREATING TYPE II DIABETES, HYPERGLYCEMIA OR HYPOGLYCEMIA BY ADMINISTERING A SYNERGISTIC COMBINATION OF A SULPHONYLUREA AND INULIN

TECHNICAL FIELD

The present invention is concerned with synergistic compositions effective in the treatment of diabetes. In particular, the present invention is concerned with synergistic compositions comprising inulin, or a suitable source thereof, and Sulphonylureas used in the treatment of type-2 Diabetes Mellitus (T2DM).

BACKGROUND OF THE INVENTION

Any discussion of the prior art throughout the specification should in no way be considered as an admission that such prior art is widely known or forms part of common general knowledge in the field.

Diabetes as a Global Health Problem (1-5):

Diabetes is the world's fastest growing chronic disease. On 20 Dec. 2006 the United Nation General Assembly passed United Nation Resolution 61/225 recognizing diabetes as a major health crisis facing all nations of the world. The Resolution designates 14 November each year as the United Nations "WORLD DIABETES DAY" and calls on all nations to develop national policies for the prevention, treatment and care of people living with diabetes and those at risk of developing diabetes.

In 2007, the five countries with the largest numbers of people with diabetes are India (40.9 million), China (39.8 million), the United States (19.2 million), Russia (9.6 million) and Germany (7.4 million). Each year a further 7 million people develop diabetes. Each year 3.8 million deaths are attributable to diabetes. An even greater number die from cardiovascular disease made worse by diabetes-related lipid disorders and hypertension. On average, people with T2DM will die 5-10 years before people without diabetes, mostly due to cardiovascular disease. Cardiovascular disease is the major cause of death in diabetes, accounting for some 50% of all diabetes fatalities, and much disability. People with T2DM are over twice as likely to have a heart attack or stroke as people who do not have diabetes. Indeed, people with T2DM are as likely to suffer a heart attack as people without diabetes who have already had a heart attack.

At least 50% of all people with T2DM are unaware of their condition. In some countries this figure may reach 80%. Up to 60% of T2DM is preventable by adopting a healthy diet and increasing physical activity.

T2DM is the largest cause of kidney failure in developed countries and is responsible for huge dialysis costs. T2DM has become the most frequent condition in people with kidney failure in countries of the Western world. 10% to 20% of people with diabetes will die of renal failure.

It is estimated that more than 2.5 million people worldwide are affected by diabetic retinopathy. Diabetic retinopathy is the leading cause of vision loss in adults of working age (20 to 65 years) in industrialized countries.

By 2025, the largest increases in diabetes prevalence will take place in developing countries. According to the International Diabetic Federation the number of individuals with diabetes will increase from 246 million at present to 380 million by 2025 (1). Due to an increasing prevalence of pre-diabetic dysglycaemia, a large number of individuals are at risk of developing T2DM particularly, due to genetic predisposition, life style and obesity (e.g. due to unhealthy diet and lack of exercise) (6).

The costs associated with the management of diabetes are 2-3 times higher than the management of other diseases, increasing from ~US$2000 (patients without diabetes) to ~US$6000 (patients with T2DM) per person. According to American Diabetes Association, in 2007, USA total direct costs associated with management of diabetes was ~US$ 116 billion with a further ~US$58 billion due to indirect costs (7).

T2DM is the sixth leading cause of death in Australia (1; 2; 4). According to Diabetes Australia, currently ~900,000 Australians are diagnosed with T2DM (8). An estimated 275 Australians develop diabetes every day. The 2005 Australian AusDiab Follow-up Study (Australian Diabetes, Obesity and Lifestyle Study) showed that 1.7 million Australians have diabetes but that up to half of the cases of T2DM remain undiagnosed (9). By 2031 it is estimated that 3.3 million Australians will have T2DM (5). The total financial cost of T2DM is estimated at $10.3 billion per annum. Of this, career costs are estimated as $4.4 billion, productivity losses are $4.1 billion, health system costs are $1.1 billion and $1.1 billion is due to obesity (3). There is no doubt diabetes is a serious health crisis. Up to 60% of cases of T2DM can be prevented by good blood glucose control, and maintaining a healthy lifestyle can significantly improve the complications associated with diabetes.

Complications Associated with Type 2 Diabetes Mellitus:

Evolution of T2DM in patients can lead to elevated risk of (i) adverse cardiovascular events, associated with atherosclerosis, particularly coronary events, (ii) retinopathy, (iii) nephropathy and (iv) neuropathy. If not treated accordingly, T2DM can result in congestive heart failure, myocardial infarction, peripheral vascular disease, stroke, pancreatitis, end stage renal disease and blindness. An increasing body of evidence suggest that these complications arise mainly due to long term HYPERGLAECEMIA and HYPERTENSION leading to loss of nutritive blood flow and damage within these organs (10). Increasing body of evidence suggest that early and effective glucose control reduces the risk of these complications in T2DM (11). Moreover, occurrence of these complications, particularly myocardial infarction and congestive heart failure, directly correlated with the increased levels of glucose and hemoglobin A1c (HAc1) in patients with T2DM (12). Remarkably, perioperative tight glycaemic control also reduce post diabetes coronary artery bypass graft complications such as mortality, infections, length of hospital stay and others factors (13) indicating elevated glucose concentrations are detrimental in long term disease manifestations as well as acute interventions and surgery. Treatment of diabetes includes oral and injectable medicines each of which has its own benefits and risks associated with the disease.

Management of Type 2 Diabetes Mellitus:

Individuals with T2DM are often prescribed tablets to control their blood glucose levels. These tablets are intended to be used in conjunction with healthy eating and regular physical activity, not as a substitute. The aim of diabetes management is to keep blood glucose levels as close to 'normal' as possible, that is between 4 to 6 mmol/L (fasting), as this will help prevent both short-term and long-term diabetic complications. Regular blood glucose monitoring is necessary to see if the treatment being followed is adequately controlling blood glucose levels.

(i) Insulin Therapy:

Insulin, a biological medicine, is infused subcutaneously to patients to exogenously elevate insulin levels in the circulation, which results in lowering glucose concentrations. However, hypoglycaemic episodes are the most common complications occurring in insulin-treated patients (14). Improvement of glycaemic control with insulin results in weight gain (~3.5 kg compared to conventional treatment at 0.4 kg), which in turn may contribute to an increased risk of cardiovascular disease and diabetes mortality (15).

(ii) Oral Treatments for T2DM:

Following tablets are currently being used for lowering blood glucose levels in T2DM. These include Biguanides, Sulphonylureas, Thiazolidinediones, Glitazones, Meglitinides, Alpha Glucosidase Inhibitor, incretin-based therapies or combinations thereof.

Although all of the agents mentioned above provide significant benefit imparted by improving glycaemic control and reducing complications, treatment with all of the agents is associated with adverse drug reactions, some of which can be serious and even life threatening. Thus, due to (i) hypoglycaemic risk in insulin and Sulphonylurea therapy, (ii) significant congestive heart failure and bone fracture episodes in thiazolidinediones, (iii) increased cardiovascular risk in rosiglitazone therapy, (iv) pancreatitis associated with Exenatide therapy, (v) lactic acidosis associated with Metformin therapy, and (vi) hypersensitivity reactions associated with sitagliptin therapy, there is a need for safer and/or more efficacious glucose lowering treatments, with improved risk-benefit profiles, to intervene with debilitating T2DM complications.

Alternative approaches to treatment of T2DM, such as for example combination therapies with dietary fiber, have also been reported. Indigestible dietary fibers, such as fructo-oligosaccharides (FOS), have long been thought to have beneficial effects on human health. To date four different clinical studies have shown contradicting results.

Effects of this class of neutraceutical in T2DM was first published in 1984 (16) demonstrating a slight reduction in blood fasting glucose levels (FGL) in patients with T2DM who were under Sulphonylurea treatment. This study showed that, in comparison to sucrose (G-F), intake of 8 gram per day for 14 days of FOS comprising a combination of Glucose-Fructose-Fructose (G-F-F), G-F-F-F and G-F-F-F-F structures, derived from treatment of sucrose with transfructosidase, resulted in ~7.6% reduction of FGL, ~7.8% reduction in total cholesterol and ~10.4% reduction of LDL-cholesterol.

FGL, total cholesterol and LDL-cholesterol were measured at the beginning (day 0) and at the end of the study (day 14). In this study, out of 14 subjects, 4 subjects showed elevated FGL whereas 10 subjects showed decreased FGL upon intake of FOS. Overall the authors suggested that the combination of FOS lower FGL in diabetic patients despite the fact that this study had (i) very minor FGL lowering effect (0.8 mmol/L reduction) (ii) increased FGL in 28.6% of the subjects (4 out of 14) and (iii) diabetic subjects with very high and uncontrolled glucose and lipid concentrations. Additionally, the study had (iv) limited scope (v) short duration (vi) and utilized several different short chain structures of FOS.

Another clinical trial (17) was conducted in 1999 on 20 T2DM patients who consumed 15 grams/day of FOS (composed of 95% FOS with degree of polymerization of 3 to 10) for 20 days. The patients were under glucose lowering medications (exact medication is unknown), anti-hypertension agents and lipid-lowering drugs. Blood was collected at the beginning (day 1) and end (day 21) of the study. The authors reported that, in comparison to placebo (D-Glucose), no significant effect of FOS on FGL was found in these patients.

A further clinical trial was published (18) on 12 patients with T2DM who were either on sulfonyleurea and/or Metformin. The authors concluded that, in comparison to placebo sucrose (G-F), treatment of T2DM with 20 gram/day of FOS (44% G-F-F, 46% G-F-F-F and 10% G-F-F-F-F purchased from ACTILIGHT, France) for 28 days did not change the patient's FGL.

US patent application US2009/0214511 purports to describe an inulin-containing digestible formulation, which also includes as essential ingredients sucrose and an amylase enzyme, that is effective in "stabilizing and balancing" blood glucose in hyperglycemic, diabetic and/or pre-diabetic patients. It also states that taking 4 grams of the formulation each day "may" improve blood glucose control. Although this patent application refers to treatment of "30 patients" with this formulation, there is no information on either the diabetic state (or otherwise) of any of the "patients", blood glucose levels of any of the patients, either before or after treatment with the formulation, or indeed any information on the type and quantity of any anti-diabetic medication that the patients may have been taking, if any was taken.

Despite the above discussed attempts to better T2DM treatment, there is still a need for alternative treatments, with more efficacious blood glucose level control and improved adverse reaction profile.

It is an objective of the present invention to overcome or ameliorate at least one of the disadvantages of the prior art treatments, or to provide a useful alternative.

SUMMARY OF THE INVENTION

According to a first aspect there is provide a method of treating diabetes comprising the administration to a subject requiring such treatment of a composition comprising inulin, or a source thereof, and a sulphonylurea, in the amount and for a time sufficient to reduce, regulate or normalize blood glucose concentration.

According to a second aspect there is provide a method of improving efficacy of sulphonylurea treatment of diabetes in a subject receiving a sulphonylurea anti-diabetic therapy, comprising administration to said subject, a composition comprising inulin or a source thereof.

Preferably diabetes to be treated is Type-2 diabetes mellitus.

According to a third aspect there is provide a method of treating hyperglycemia in a subject comprising the administration to the subject requiring such treatment of a composition comprising inulin, or a source thereof, and a sulphonylurea, in the amount and for a time sufficient to reduce, regulate or normalize blood glucose concentration.

Preferably the subject has mild hyperglycemia which represents a pre-diabetic state.

Importantly, inulin is able to prevent or ameliorate hypoglycaemia frequently associated with sulfonylurea treatment.

According to a fourth aspect there is provide a method of preventing the development of, or ameliorating, hypoglycaemia in a subject treated with a sulphonylurea, comprising the administration to a subject requiring such treatment of a composition comprising inulin or a source of inulin, in the amount and for a time sufficient to prevent or ameliorate hypoglycemia.

Inulin may be used in pure or purified form but may also be conveniently provided in form of a plant preparation or extract rich in inulin. Such plant sources may be advantageously selected from onion, leek, garlic, artichoke, salsify, agave and chicory.

The Sulphonylurea may be selected from Gliclazide, Glisoxepide, Glibenclamide (known also as Glyburide), Glipizide, Glimepiride, Gliquidone, Glyclopyrimide, Tolazamide, Tolbutamide, Chlorpropamide, Acetohexamide or combinations thereof.

The preferred combination treatment is that which makes use of Glibenclamide or Gliclazide and inulin from chicory root (CR), or food-grade inulin, as a convenient sources of relatively pure inulin. It will be understood, of course, that other sources of inulin, or purified or synthetic inulin, may also be used in the compositions and methods of the present invention, as can other Sulphonylureas.

Inulin, or a source thereof, may be administered simultaneously or sequentially, in any order, with a Sulphonylurea. The preferred route of administration is oral.

Conveniently, inulin may be administered as a supplement in daily meals or beverages. However, it is preferred that inulin is administered in a pharmaceutical unit dosage form such as pills, tablets, caplets, tapsules or capsules, for better control of dosing and patient compliance.

According to a fifth aspect the present invention provides a synergistic composition comprising inulin, or a source thereof, and a sulphonylurea.

Whereas such a combination may be formulated into a conventional tablet or capsule form, it is preferred that it is formulated into immediate, sustained or delayed release formulations.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

DESCRIPTION OF THE PREFERRED EMBODIMENT

Figure 1:
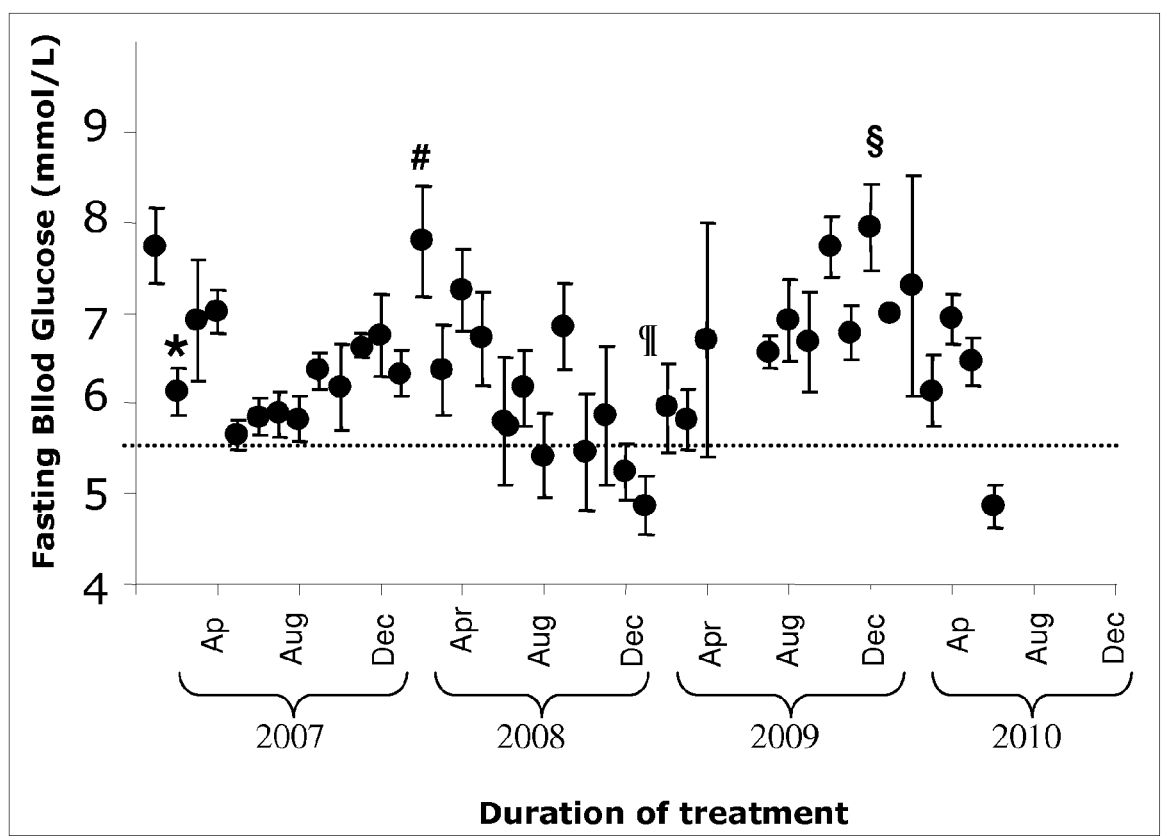
FIG. 1: FBG during Glibenclamide and inulin intake. The patient has consumed inulin (JLS) at specified amounts and the FBG were measured as described in the Examples. Error bars represent average±Standard Error of the Mean (SEM) of FBG levels within the specified month. Figure legend:
* Glibenclamide dose increased from 10 to 15 mg per day.
patient consumed 12 gr/day of inulin.
¶ Inulin discontinued.
§patient recommences consuming 12 gr/day of inulin.

Sulphonylureas are most widely used in regulating blood glucose levels and are used extensively in the treatment of Type 2 Diabetes Mellitus (T2DM). These agents have a reasonably good safety profile in that their long term use does not harm tissues and organs. However, Sulphonylureas can cause hypoglycemia, which can be fetal. One such agent, Glibenclamide, was developed in 1966 and used extensively in the treatment of T2DM. By inhibiting ATP-dependent potassium channels in pancreatic β islets, Glibenclamide triggers increased insulin secretion. This property and mechanism of action is shared by other sulphonylureas. For unknown reasons, however, after some months/years of therapy patients become resistant to Glibenclamide therapy. This is also observed with other sulphonylueras such as Gliclazide and, based on similarity in their mode of action and chemical structure, it will be understood that other Sulphonylureas will exhibit similar resistance through prolonged usage. Therefore other means of combination therapy, which improves the efficacy of Sulphonylureas, is required to control glucose levels.

In contrast to the published reports to date, it has now been surprisingly found that treatment with a combination of Sulphonylurea (for example Glibenclamide, or Gliclazide) and inulin or a source of inulin, such as CR or similar inulin-rich plant source, acts synergistically to normalize blood glucose levels in a patient with T2DM. Based on similarity in their mode of action and chemical structure it will be understood that other members of the sulphonylurea family will also exhibit such synergistic action with inulin. The study remarkably demonstrated that inulin, or a natural product containing inulin (e.g. CR), may be widely used in combination therapy to maintain lower, or normalize, blood glucose levels and thus minimize the complications associated with high blood glucose levels. The present studies also indicate that inulin or a source thereof may be effective in preventing or ameliorating adverse drug reactions, such as hypoglycemia, caused by Sulphonylurea treatment. Moreover, inulin combination therapy will permit a reduction in the patient's prescribed dose of Sulphonylurea to regulate blood glucose levels. The adjustment in the quantum of anti-diabetic medication is frequently done by medical practitioners in the course of managing a diabetic patient and would be motivated by normalization of the patient's blood glucose levels following combination treatment with inulin. These in turn will further minimize the potential adverse drug reactions associated with the Sulphonylurea therapy.

Inulin appears to be acting synergistically with Sulphonylurea in a dose-dependent manner, to normalize blood glucose concentrations in a patient, thus improving the efficacy of sulphonylurea treatment of diabetes and hyperglycaemia. Interestingly, other biochemical parameters of relevance, including HA1c, cholesterol, triglycerides, LDL, HDL and coronary risk ratios also appear to be improved by such treatment.

The amount of inulin that may typically be used orally, and shows good efficacy in combination therapy, will be easily determined by a medical practitioner, depending on the source of inulin, the patient's condition and response, type of anti-diabetic treatment and the like, and will typically be in the range from about 4 grams/day to about 40 grams/day (or its inulin equivalent weight of preparations containing inulin), and more typically 10 to 35 grams/day. A convenient dose may be selected from 4, 6, 8, 10, 11, 12, 13, 14, 15, 16, 17, 18, 19, 20, 21, 22, 23, 24, 25, 26, 27, 28, 29, 30, 32, 34, 36, 38 or 40 grams/day, depending on the patient's response and the source of inulin. This is easily determined by simple trial and error with respect to dosage adjustment. Further, depending on the route of administration the dosage regimen may also differ (e.g. IV administration may require lesser amounts). Lower doses of inulin may be used if only minor effects on FBG are desired or in situations where low dose sulphonylurea is used. Higher doses of inulin may also be used and are effective but may be associated with mild discomfort. The inulin containing composition may be administered simultaneously with Sulphonylureas or it may be administered sequentially in any order. Further, the daily, weekly or monthly dose of inulin may be divided and taken in several smaller doses or may be taken as a bolus dose. A suitable and convenient dosing regimen would be, for example, administering one-third of the total daily dosage during or immediately after each breakfast, lunch and dinner.

In addition to pure, purified or synthetic inulin, natural sources of inulin other than CR described above may be selected from inulin-rich plants such as for example onion, leek, garlic, artichoke, salsify, agave and the like. Other inulin-rich plant sources can be easily ascertained by those skilled in the art. The approximate amounts and degree of polymerization of inulin in these plant sources are listed in Table 1 (19).

TABLE 1

Content and degree of polymerization of inulin in plant sources.

| Source | Inulin content (% of fresh weight, w/w) | Degree of polymerization (DP) |
|---|---|---|
| Onion | 2-6 | 2-12 (Average 5) |
| Jerusalem artichoke | 14-19 | 2-50 (52% DP < 10, 22% DP10-20, 20% DP20-40, 6% DP > 40 |
| Chicory | 15-20 | 3-60 (31% DP < 10, 24% DP10-20, 45% DP > 20 |
| Leek | 3-10 | 12 |
| Garlic | 9-16 | 2-50 |
| Artichoke | 3-10 | (0% DP < 19, 13% DP19-40, 87% DP > 40) |
| Wheat | 1-4 | Low DP range, DP < 5 |
| Banana | 0.3-0.7 | ND |
| Rye | 0.5-1 | ND |
| Barley | 0.5-1.5 | ND |
| Dandelion | 12-15 | ND |
| Burdock | 3.5-4.0 | ND |
| Camas | 12-22 | ND |
| Murnong | 8-13 | ND |
| Yacon | 3-19 | ND |
| Salsify | 4-11 | ND |

ND, Not Determined

Inulins obtained from natural sources typically have a heterogeneous degree of polymerization (DP). For example, inulin obtained from CR has a DP range of from 3 to about 60 (with average DP of 25), or about 8 to about 60 with a similar average DP. In that regard it will be noted that inulins from these natural sources will also contain a proportion of fructooligosaccharide (FOS), which typically are in the DP range of 3 to 10. Commercial sources of inulin are well known, as described in the examples herein.

Advantageously, inulin or a natural source thereof may be used in combination with any Sulphonylurea which is effective in regulating blood glucose concentration and may be selected from, for example, Gliclazide, Glisoxepide, Glibenclamide (known also as Glyburide), Glipizide, Glimepiride, Gliquidone, Glyclopyrimide, Tolazamide, Tolbutamide, Chlorpropamide and Acetohexamide. The amount of Sulphonylurea administered to a patient may be varied, including reduced, depending on patient's response to combined treatment with inulin or a natural source thereof.

Inulin or a natural source thereof may be administered to a patient receiving a Sulphonylurea agent either at the start of treatment with Sulphonylurea, and administration continued for as long as the patient is treated with Sulphonylurea, or may be administered intermittently as required to regulate/normalize blood glucose levels. The effect of co-administration of inulin and a Sulphonylurea on blood glucose levels may not be seen in the short term and hence co-administration may need to be maintained for a period of time long enough to achieve the desired effects, for example in excess of 2 to 3 months and preferably 4 to 6 months. Based on the patient's condition, nature of treatment and response, longer periods of administration of inulin may be required before beneficial effects are noted. Of course it will be understood that such co-administration may be maintained for as long as the patient requires treatment for diabetes or hyperglycaemia.

The compositions of the present invention may be In addition to being effectively used in the treatment of patients with T2DM, the compositions of the present invention may also be used to treat subjects with hyperglycemia who are not yet classified as diabetic (i.e. pre-diabetic) but who are nevertheless on low level sulphonylurea treatment, so as to prevent or delay onset of diabetes.

The compositions of the present inventions can be administered by a variety of routes including oral, rectal, transdermal, subcutaneous, intravenous, intramuscular, intrathecal, intraperitoneal, intranasal and buccal. Depending on the intended route of delivery, the compounds are preferably formulated as either oral, injectable or topical compositions.

The compositions for oral administration may take the form of bulk liquid solutions or suspensions, or bulk powders and the like. For example, in case of inulin or a natural source thereof, the compositions can be in the form of a food supplement, for example a powder or a suspension that can be simply added to daily meals before consumption. It may also take the form of fresh, dried or semi-dried parts of plants, to be used in a similar manner.

More preferably, however, the compositions are presented in unit dosage forms to facilitate accurate dosing. The term "unit dosage forms" refers to physically discrete units suitable as unitary dosages for human subjects and other mammals (for example companion animals or stock animals), each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules, caplets, tapsules or the like, in the case of solid compositions.

The agents or compounds of the present invention may be prepared as separate compositions, for either sequential or simultaneous administration, or may be formulated together in a combination composition/unit dosage form. Such compositions, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For certain applications the compositions may also be in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient(s) commensurate with the intended daily, weekly, monthly or other dosage range to be employed. Injectable compositions are typically based upon injectable sterile saline or phosphate-buffered saline or other injectable carriers known in the art.

The amount of each composition actually administered will typically be determined by a physician in the light of the relevant circumstances, including the condition to be treated, the chosen route of administration, the actual compound(s) administered, the age, weight, and response of the individual patient, the severity of the patient's symptoms/condition, and the like.

The above described components for orally administered or injectable compositions are merely representative. Further materials as well as processing techniques and the like are set out in Part 5 of Remington's Pharmaceutical Sciences (20).

The compounds of the present invention can also be administered in sustained release forms or from sustained release drug delivery systems, either in separate dosage forms or in a combination dosage form. A description of representative sustained release materials can also be found in the incorporated materials in Remington's Pharmaceutical Sciences.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1

Glibenclamide/Inulin Combination Therapy for Type 2 Diabetes Mellitus: A Case Report (i) Synopsis This study on a T2DM patient being treated with a sulphonylurea, Glibenclamide, demonstrates a profound efficacy of inulin on normalization of FBG. This patient showed resistance to Glibenclamide therapy (15 mg/day). Remarkably consumption of inulin in combination with Glibenclamide resulted in a synergistic effect in that it lowered and kept FBG at normal levels in a dose dependent manner with respect to inulin. Furthermore, withdrawal of inulin resulted in elevated FBG but reintroduction of inulin again normalized the FBG. The patient observed that inclusion of inulin provided energy restoration, ease in muscle pain and better life style and most importantly elimination of hypoglycemic episodes. Normalization of FBG also assisted the patient in coping with her cataract and bladder incontinence surgeries. These findings suggest a direct relationship between inulin consumption, and FBG when used in combination with Glibenclamide.

(ii) Background:

Elevated blood glucose level is the hallmark of debilitating disease such as T2DM. In this disease the patient's cells fail to take up insulin or release insulin which is required to regulate blood glucose levels. Increased glucose levels act as inflamasomes to activate the immune system and cytokine production (21). White blood cells also destroy β islets in pancreas resulting in diminished insulin production. Elevated glucose levels in turn results in many disease manifestations and several organ damage and ultimately death. There are a handful of medicines that are successfully used to treat T2DM.

As mentioned earlier, Glibenclamide inhibits ATP-sensitive potassium channels in pancreatic β islets, resulting in increased insulin secretion, a mechanism of action similar to that of other sulphonylureas. Due to development of resistance to sulphonylurea treatment other means of combination therapy are required to control glucose levels. This lead to the present studies which demonstrate synergistic blood glucose lowering ability of inulin and Glibenclamide, as an example of a sulphonylurea. The data shows that although patient become resistant to Glibenclamide therapy alone, inclusion of inulin profoundly controls the FBG, lowering it to normal levels and ameliorating Glibenclamide-mediated hypoglycaemia. This synergistic effect dramatically improved patient's overall life style who also suffered from other illnesses such as atrial fibrillation, high blood pressure, high blood cholesterol and osteoarthritis.

(iii) Subject:

64 years old female, with body mass index of 32 classified as obese, with the history of T2DM, atrial fibrillation, high blood pressure, high blood cholesterol and osteoarthritis.

Medical History:

At the age of 49 the patient, who lived in north-east of Iran, was diagnosed with T2DM. Doctor recommended diet-only treatment. At age 51 due to increased FBG and high blood pressure the patient was treated with Glibenclamide (5 mg/day, 2×2.5 mg/day) and Captopril (5 mg per day). At age 60 the patient hospitalized due to high blood pressure and heart failure. She was treated and prescribed with nitro-glycerine and Metoprolol (AstraZeneca Pty Ltd, Australia). Currently the patient is under the following medications:

Prescription Medicines:

| Glibenclamide (Alphapharm Pty Ltd): | 15 mg/day | 5 mg - 3 times a day |
|---|---|---|
| Captopril (Alphapharm Pty Ltd): | 50 mg/day | 25 mg - 2 times a day |
| Sotalol (Sandoz Pty Ltd): | 80 mg/day | 40 mg twice a day |
| Atorvastatin (Pfizer): | 40 mg/day | 40 mg once a day |

OTC or Other Supplements:

| Inulin: | 12 grams/day | 4 grams - 3 times a day |
|---|---|---|

Inulin sources: Inulin, from Chicory root (CR), was obtained in the form of a product named Just Like Sugar® (Just Like Sugar, Inc., P.O. Box 96083, Las Vegas, Nev. 89193, USA; Product Code: AR160GR-2) which contains, inter alia, about 96% inulin and was used as a suitable source of inulin for the present studies. This source of inulin will be referred to where appropriate as inulin (JLS). Typically, inulin extracted from CR has a heterogeneous DP, ranging from about 3 to about 60, with average DP of about 25 (19; 22).

Another inulin preparation used in the present studies was sourced from Orafti Inc., Belgium (DP in the range from about 8 to about 60, with average DP of about 25). This source of inulin will be referred to where appropriate as inulin (Orafti).

(iv) Methods:

Glucose measurements: Blood glucose level was determined using Accu-Chek Advantage (Roche, Mannheim, Germany) device (CAT/TYP 033304394001 mmol/L and 8549084416) according to manufacturer instructions. Other similar devices can also be used. All other tests for which data is provided herein were performed by SADRA pathology laboratory in north-east of Iran or MEDLAB pathology laboratory in Australia.

(v) Results:

The efficacy of inulin on Glibenclamide therapy was investigated. Several years prior to inulin combination therapy, patient's FBG fluctuated drastically and was uncontrolled around 10 mmol/L. Her cholesterol and triglyceride were also very high (Table 2). FIG. 1 depicts the monthly FBG average at indicated time points. Conditions of treatments are described below:

January 2007: Patient's endocrinologist increased the Glibenclamide dose from 2×5 mg to 3×5 mg per day. As a result the patient responded to dose increase and her FGL substantially decreased from 7.8 mmol/L (average FBG in January) to 6 mmol/L (average FBG in February).

March-August 2007: In the next several months following the increase in Glibenclamide dosage, the patient's FBG continued to fluctuate and increase.

September 2007-January 2008: The patient began to consume low doses of 4.5 grams/day of inulin (JLS).

January-February 2008: Consumption of inulin gradually increased to 12 grams/day.

March-August 2008: Increased inulin intake resulted in gradual decline of FBG to a healthy limit. i.e. below 5.5 mmol/L.

September 2008: Patient hospitalized due to heart palpitation. For the first time she was diagnosed with Atrial fibrillation and prescribed with Warfarin. Her FBG fluctuated during this month but declined to normal levels in October and persisted until March 2009.

December 2008: Patient had a cataract surgery. Low FBG assisted in an excellent recovery.

January 2009: Patient had a surgery to alleviate bladder incontinence. Low FBG assisted in excellent recovery.

March 2009: Inulin supply became unavailable. By October 2009 patient's FBG substantially increased to ~7.5 mmol/L.

October 2009: Patient began to consume inulin at ~3.5 grams/day.

April 2010: Consumption of inulin increased to 12 grams/day.

Although FBG fluctuated depending on the amount of inulin consumed, the patient exhibited normal levels of HA1c and lipid profiles (Table 2).

TABLE 2

FBG, HA1c and lipid profiles of the patient performed by an independent pathology laboratory.

|  | Nov. 5, 2006* | May 31, 2008# | Oct. 1, 2008 | Dec. 12, 2008 | Oct. 24, 2009 | Mar 2, 2010 | Mar. 7, 2010 | Apr. 27, 2010 | Jan. 17, 2011 |
|---|---|---|---|---|---|---|---|---|---|
| Fasting Glucose (Normal 3-5.5 mmol/L) | 10 | 6 | 6.3 | 5.1 | 7 | 6.4 |  |  | 5.4 |
| HA1c (Normal <7%) |  | 6.5 | 7 |  | 6.6 |  | 6.9 | 6.9 | 6.8 |
| Cholesterol (Normal 3.1-5.1 mmol/L) | 6.2 | 3.1 | 3.6 | 3.8 | 4.4 | 4.4 |  |  | 3.8 |
| Triglyceride (Normal 0.5-2 mmol/L) | 4 | 1.1 | 1 | 1 | 1 | 1.6 |  |  | 1.5 |
| HDL (Normal >1 mmol/L) |  | 1.2 | 1.2 |  | 1.4 | 1.3 |  |  | 1.1 |
| LDL (Normal 0-3.5 mmol/L) |  | 1.4 | 1.9 |  | 2.5 | 2.4 |  |  | 2.0 |
| Coronary risk ratio (Normal <5) |  | 2.6 | 3 |  | 3.1 | 3.4 |  |  | 3.4 |

*Tests on this date have been performed by SADRA Pathology Laboratory in Iran
Tests from 2008 to date have been performed by MEDLAB Pathology in Australia (vi) Conclusions:

The FGL of the patient is restored to near normal levels when inulin consumed at approximately 12 grams/day in combination with Glibenclamide. The patient also claims that consumption of inulin boosted her energy, reduced hypoglycemic episodes, alleviated her muscle pains and overall provided a better quality daily life.

Example 2

Figure 2:
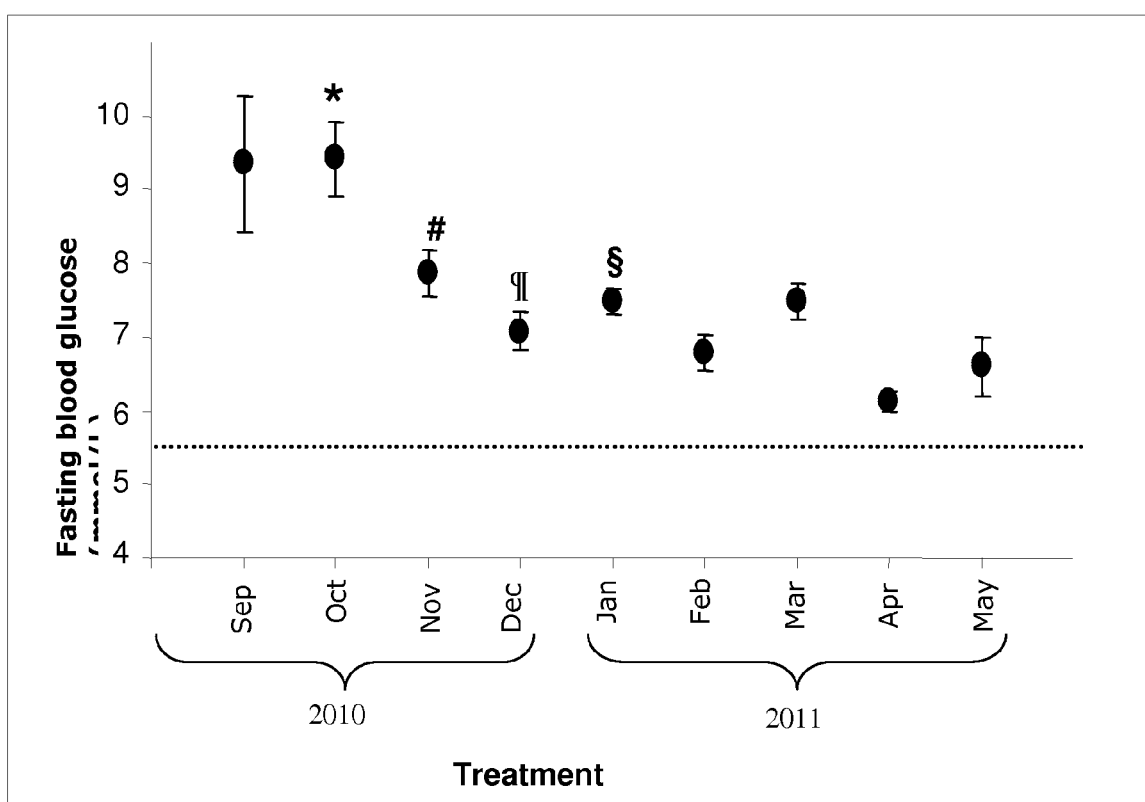
FIG. 2: Dose and time dependency of inulin effect on FBG levels in a patient on Gliclazide monotherapy. Figure legend:
* Inulin (JLS) dose escalation.
patient consumed 9 gr/day of inulin (JLS).
¶ patient consumed 12 gr/day of imulin (JLS).
§patient consumed 15 gr/day of inulin (JLS).

Gliclazide/Inulin Combination Therapy for Type 2 Diabetes Mellitus: A Case Report Another patient, who was under Gliclazide therapy (30 mg, once daily) for nearly a decade with uncontrolled blood glucose levels above 9 mmol/L, also began the combination therapy with inulin (JLS). Various blood parameter measurements were as described in Example 1. The results are shown in FIG. 2. Consumption of 9 gram per day of inulin, while carrying on the gliclazide therapy, resulted in a reduction of FBG level from 9.4±1.82 mmol/L to 7.5±0.2 mmol/L and reduced fluctuation of FBG ($p<0.016$, error bars represent standard error mean of 12-15 FBG measurements in a given month). Consumption of 12 gr per day of inulin resulted in further reduction of patient's FBG levels to 7.1±0.1 mmol/L. Continuing combination treatment with this amount of inulin resulted in further reduction of FBG to 6.2±0.1 mmol/L, a further reduction in glucose fluctuation.

TABLE 3

FBG, HA1C and Lipid profiles of the patient performed by an independent pathology laboratory.

|  | Jul. 22, 2008* | Apr. 20, 2009* | Dec. 17, 2010# | May 16, 2011* |
|---|---|---|---|---|
| Fasting Glucose (Normal 3-5.5 mmol/L) | 6.0 | 7.7 | 7.4 | 5. |
| HA1c (Normal <7%) | 7. | 7. | 7.8 | 7.2 |
| Cholesterol (Normal 3.1-5.1 mmol/L) | 4.4 | 4.2 | 2.9 | 4.4 |
| Triglyceride (Normal 0.5-2 mmol/L) | 1. | 1. | 0. | 1.2 |
| HDL (Normal >1 mmol/L) | 1.0 | 1.2 | 1.1 | 1. |
| LDL (Normal 0-3.5 mmol/L) | 2.9 | 2.3 | 1.4 | 2. |
| Coronary risk ratio (Normal <5) | 4.4 | 3.5 | 2.6 | 3.7 |

*Tests on this date have been performed by Douglas Hanly Moir Pathology.
Tests on this date have been performed by MEDLAB Pathology.

Example 3

Glibenclamide/Inulin Combination Therapy for Type 2 Diabetes Mellitus: Using Different Source of Inulin The patient, as described above in Example 1, was switched over to inulin (Orafti), and combination therapy with Glibenclaminde (5 mg, three times daily) continued following a similar protocol as described above except that the patient received 15 gr/day of inulin (Orafti). Over a two month period FBG levels rose above normal levels but when the dosage was increased to 22 gr/day the FBG levels plateaued. Following a further escalation of inulin dosage to 30 gr/day the FBG returned to normal levels.

Figure 3:
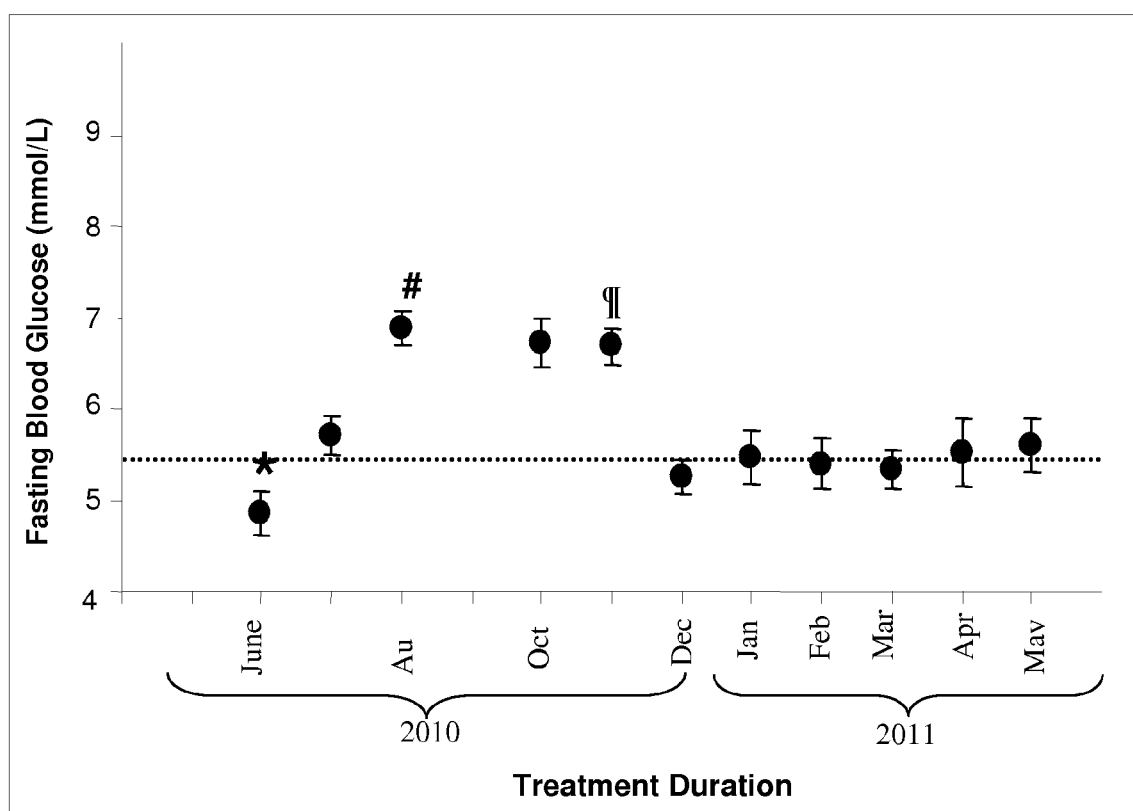
FIG. 3: Effect of inulin on FBG levels in a patient on treatment with sulfonylurea, Glibenclamide, mono therapy. Figure legend:
* Inulin (JLS) switched to 15 gr/day of inulin (Orafti).
patient consumed 22 gr/day of inulin (Orafti).
¶ patient consumed 30 gr/day of inulin (Orafti).
Figure 4:
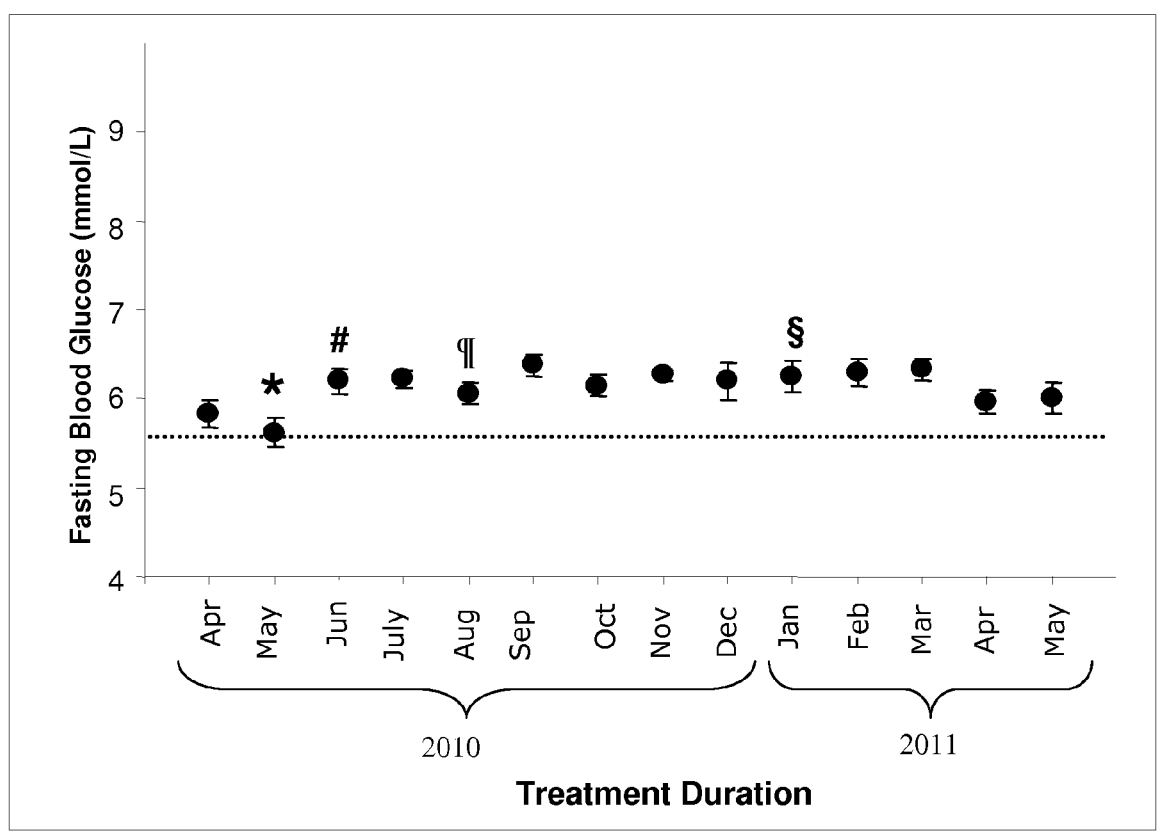
FIG. 4: Effect of inulin on a pre-diabetic subject who is not under any anti-diabetic regimen. Figure legend:
* Inulin (JLS) dose escalation.
subject consumed 12 gr/day inulin (JLS).
¶ subject consumed 12 gr/day inulin (Orafti).
§subject consumed 12 gr/day inulin (JLS).

Consumption of inulin (Orafti) preparation, similar to what was observed with inulin (JLS), resulted in keeping FBG at normal levels. Maintaining the patient on combination therapy with this inulin preparation has normalized the FBG levels and maintained them within the normal range. The results of this study are shown in FIG. 3.

Example 4

Effect of Inulin on FBG in a Pre-Diabetic Subject

A subject who was predisposed to diabetes (his mother has type 2 diabetis mellitus) but under no anti-diabetic medication, and who had FBG levels above normal limits (approx. 6.0 mmol/L), also consumed inulin, first inulin (JLS) then inulin (Orafti), for 13 months. In contrast to patients who were under sulfonylurea treatment, the consumption of 12-15 gr/day of inulin over the period of 13 months did not change the levels of FBG in this subject.

Example 5

Figure 5:
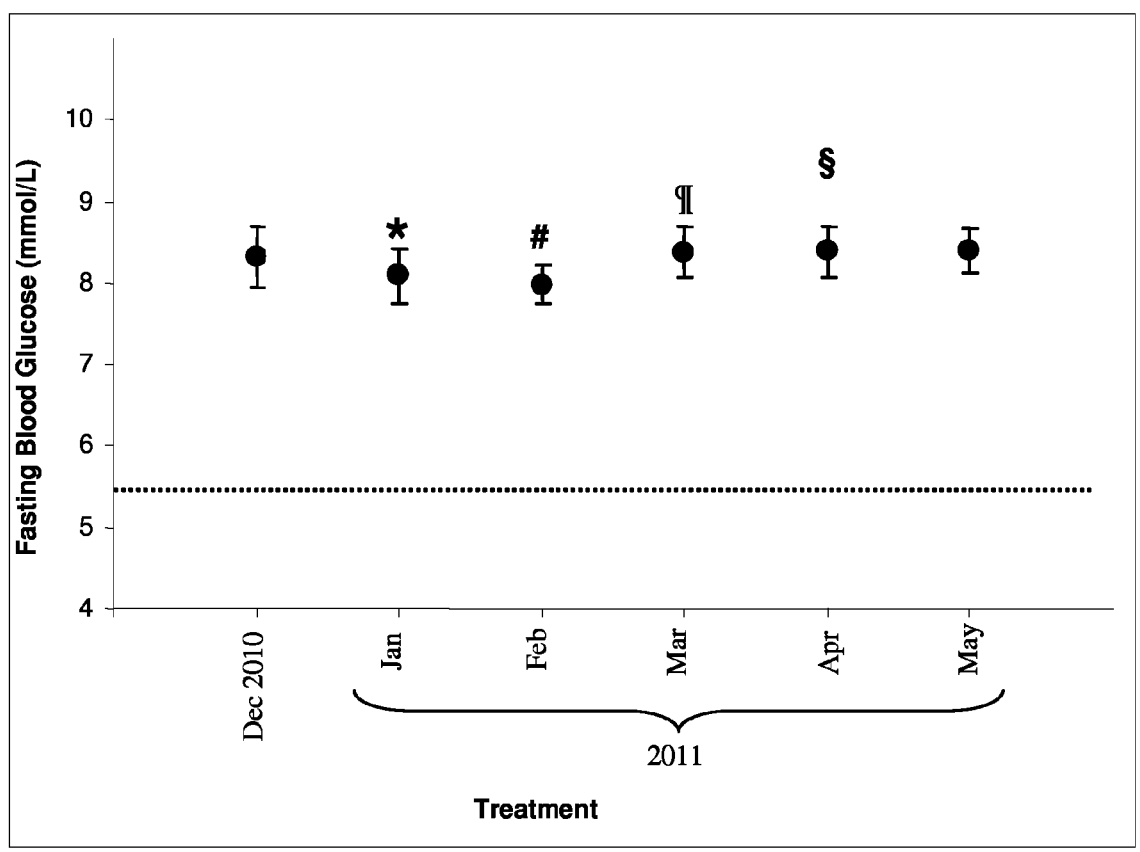
FIG. 5: Effect of inulin on FBG levels in a patient who is on Metformin, Glucobay and insulin combination therapy. Figure legend:
* Inulin (JLS) dose escalation.
patient consumed 12 gr/day inulin (JLS).
¶ patient consumed 15 gr/day inulin (JLS).
§patient consumed 12 gr/day inulin (JLS).

Effect of Inulin on FBG of a Diabetic Patients Treated with Non-Sulphonylurea Anti-Diabetic Medication In a patient who was on anti-diabetic treatment with a combination of Metformin (500 mg twice daily), Glucobay (100 mg, three times a day) and insulin (60 units twice daily), the inulin dose was escalated in January 2011 and therapeutic dose of 12 gr/day initiated on February 2011. Doses of 12-15 gr/day of inulin (JLS) for 4 months did not affect the FBG levels in this patient (see FIG. 5). It appears that inulin does not synergize with Metformin and/or Glucobay in regulation of FBG in diabetic patients.

TABLE 4

FBG, HA1C and Lipid profiles of the patient performed by an independent pathology laboratory.

|  | Apr. 1, 2010* | Jul. 26, 2010* | Sep. 11 2010* | Nov. 30, 2010* | Feb. 26, 2011* |
|---|---|---|---|---|---|
| Fasting Glucose (Normal 3-5.5 mmol/L) |  |  | 10.7 | 8.6 | 8. |
| HA1c (Normal <7%) | 8.0 | 7. | 7.0 | 7.3 | 7. |
| Cholesterol (Normal 3.1-5.1 mmol/L) | 5.1 | 4.4 | 4.8 | 5.1 | 5.0 |
| Triglyceride (Normal 0.5-2 mmol/L) | 2.7 | 1. | 0.9 | 1.4 | 1. |
| HDL (Normal >1 mmol/L) | 1.3 | 1. | 1.5 | 1.5 | 1. |
| LDL (Normal 0-3.5 mmol/L) | 2.6 | 2. | 2.9 | 3.0 | 2. |
| Coronary risk ratio (Normal <5) | 3.9 | 3.1 | 3.2 | 3.4 | 3.6 |

*Tests on this date have been performed by MEDLAB Pathology in Australia

Figure 6:
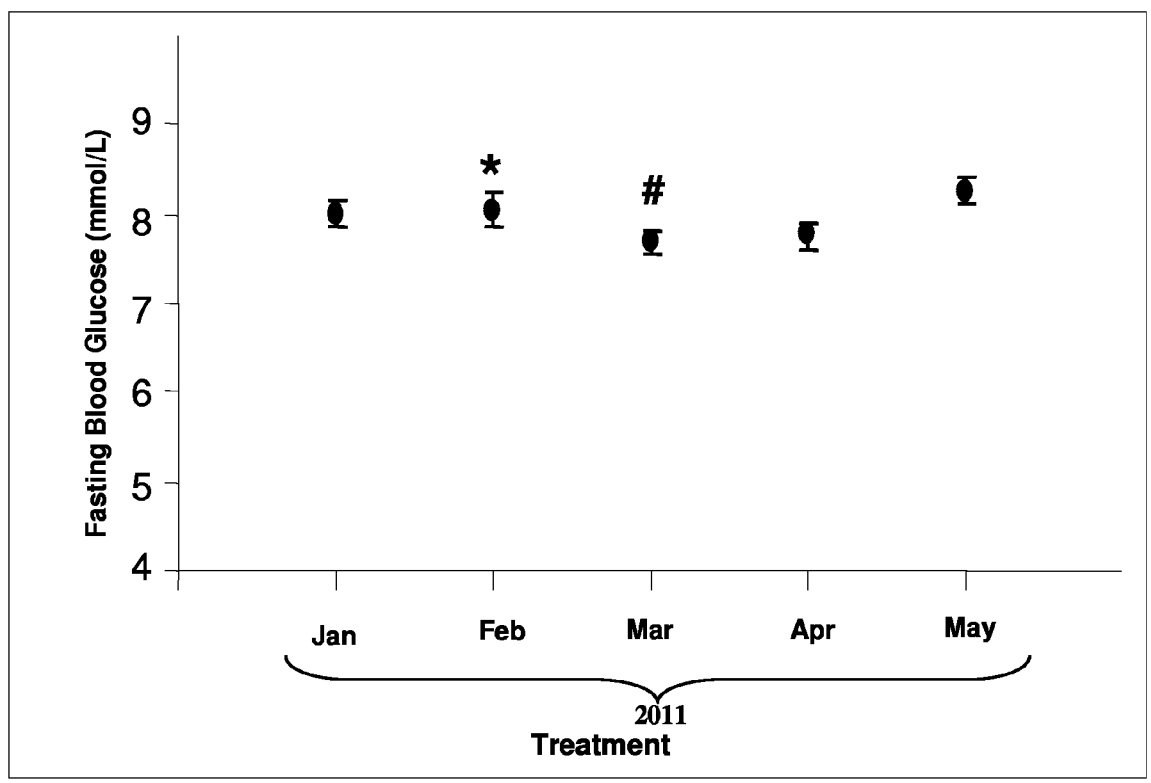
FIG. 6: Effect of inulin on FBG levels in a patient who was on Metformin and Pioglitazone combination therapy. Figure legend:
* Inulin (JLS) dose escalation.
patient consumed 12 gr/day inulin.

In another patient who was on Metformin (1000 mg twice daily)/Pioglitazone (15 mg once daily) combination anti-diabetic treatment, the inulin dose escalation was started on February 2011 and continued for the following three months with a therapeutic dose of 12 gr/day of inulin (see FIG. 6), but with no significant effect on FBG. From this study it appears that inulin also shows no synergy with another non-sulphonylurea anti-diabetic medication, Pioglitazone.

TABLE 5

FBG, HA1C and Lipid profiles of a patient (MR) performed by independent Pathology laboratories

|  | Jun. 4, 2009* | Nov. 26, 2009* | May 22, 2010* | Jan. 29, 2011* |
|---|---|---|---|---|
| Glucose (Normal 3-5.5 mmol/L) | 9.0 | 8.6 | 12 | 7.8 |
| HA1c (Normal <7%) | 7.2 | 7.7 | 7.2 | 7.5 |
| Cholesterol (Normal 3.1-5.1 mmol/L) | 5.4 | 5.6 | 3.0 | 2.8 |
| Triglyceride (Normal 0.5-2 mmol/L) | 1.2 | 1.7 | 0.9 | 1.1 |
| HDL (Normal >1 mmol/L) | 1.4 | 1.4 | 1.7 | 1.5 |

TABLE 5-continued

FBG, HA1C and Lipid profiles of a patient (MR) performed by independent Pathology laboratories

|  | Jun. 4, 2009* | Nov. 26, 2009* | May 22, 2010* | Jan. 29, 2011* |
|---|---|---|---|---|
| LDL (Normal 0-3.5 mmol/L) | 3.4 | 3.4 | 0.9 | 0.8 |
| Coronary risk ratio (Normal <5) | 3.8 | 4 | 1.8 | 1.9 |

*Tests on this date have been performed by MEDLAB Pathology in Australia

Unlike sulphonylureas, Glucobay is a competitive inhibitor of intestinal alpha-glucosidases with maximum specific inhibitory activity against sucrose. Under the influence of Glucobay, the digestion of starch and sucrose into absorbable monosaccharides in the small intestine is dose-dependently delayed. Also unlike sulphonylureas, Metformin (a biguanide) acts on the liver and decreases hepatic gluconeogenesis and release of glucose into the blood stream. Further, Pioglitazone, unlike sulphonylureas, selectively stimulates the nuclear receptor peroxisome proliferator-activated receptor gamma (PPAR-$\gamma$) and to a lesser extent PPAR-$\alpha$. It modulates the transcription of the insulin-sensitive genes involved in the control of glucose and lipid metabolism in the muscle, adipose tissue and the liver. None of these compounds act on the pancreas to stimulate insulin secretion as do sulphonylureas.

These studies demonstrate that inulin consumption by patients suffering from chronic T2DM reverses resistance to sulphonyluera therapy, lowers the FGB to normal levels and eliminates hypoglycemic episodes. The findings indicate that inulin and sulphonylureas act synergistically in lowering FGB in T2DM patients. On the other hand, inulin had no effect on FBG when administered for a prolonged period to a pre-diabetic subject having elevated FBG or to diabetic patients on anti-diabetic medication that does not include a sulphonylurea.

Although the invention has been described with reference to specific embodiments it will be understood that variations and modifications in keeping with the principles and spirit of the invention described are also encompassed.

REFERENCES

1. Diabetes Atlas, Third edition, International Diabetes Federation, 2007.
2. Diabetes and Cardiovascular Disease: Time to Act, International Diabetes Federation, 2001.
3. The Economic Costs of Obesity, 2006.
4. World Health Organisation Diabetes Unit.
5. http://www.diabetesaustralia.com.au/en/Understanding-Diabetes/Diabetes-in-Australia/.
6. Sicree R: Diabetes Atlas, Third Edition. *International Diabetes Federation, Brussels,* 2008
7. Zimmet P: Preventing diabetic complications: A primary care perspective. *Diabetes Research and Clinical Practice* 84:107-116, 2009
8. www.ndss.com.au:
9. AusDiab Report, 2006.
10. Wiernsperger N, Bouskela E: Microcirculation in insulin resistance and diabetes: more than just a complication. *Diabetes Metab.* 29:6S77-87, 2003
11. Holman R, Paul S, Bethel M, Matthews D, Neil H: 10-year follow-up of intensive glucose control in type 2 diabetes. *N Engl J Med.* 359:1577-1589, 2008
12. Bergenstal R, Bailey C, Kendall D: Type 2 diabetes: assessing the relative risks and benefits of glucose-lowering medications. *Am J Med.* 123:9-18, 2010
13. Furnary A, P: Clinical Benefits of tight glycaemic control: Focus on the perioptive setting. *Best Practice & Research Clinical Anaesthesiology* 23:411-420, 2009
14. Bailey C, Campbell I, Chan C, et al.: Metformin: The gold standard. Chichester, UK; Hoboken, N.J.: John Wiley & Sons, 2007
15. Hermansen K, Mortensen L: Bodyweight changes associated with antihyperglycaemic agents in type 2 diabetes mellitus. *Drug Saf.* 30:1127-1142., 2007
16. Yamashita K, Kawai K, Itakura M: Effects of fructo-oligosaccharides on blood glucose and serum lipids in diabetic subjects. *Neutrition Res* 4:961-966, 1984
17. Alles M, de Roos N, Bakx J, van de Lisdonk E, Zock P, Hautvast G: Consumption of fructooligosaccharides does not favorably affect blood glucose and serum lipid concentrations in patients with type 2 diabetes. *Am J Clin Nutr.* 69:64-69, 1999
18. Luo J, Van Yperselle M, Rizkalla S, Rossi F, Bornet F, Slama G: Chronic consumption of short-chain fructooligosaccharides does not affect basal hepatic glucose production or insulin resistance in type 2 diabetics. *J Nutr.* 130:1572-1577, 2000
19. van Loo J, Coussement P, de Leenheer L, Hoebregs H, Smits G: On the presence of inulin and oligofructose as natural ingredients in the western diet. *Crit Rev Food Sci Nutr.* 35:525-552, 1995
20. Remington's Pharmaceutical Sciences, Mack Publishing Company, Easton, Pa., USA 20.sup.th Edition, 2000
21. Jin C, RA F: The missing link: how the inflammasome senses oxidative stress. *Immunology and Cell Biology advance online publication* doi:10.1038/icb.2010.56 2010
22. Ritsema T, Smeekens S: Fructans: beneficial for plants and humans. *Curr Opin Plant Biol.* 6:223-230, 2003

The claims defining the invention are as follows:

1. Method of treating Type-2 diabetes mellitus comprising the administration to a subject requiring such treatment of a composition comprising inulin, or a source thereof which contains inulin, and administration of an effective amount of a sulphonylurea, wherein the inulin is administered in an amount of from about 4 grams/day to about 35 grams/day and in an amount and for a time sufficient to improve a reduction, regulation or normalization of blood glucose concentration compared to treatment with said same sulphonylurea without inulin, and wherein the sulphonylurea is selected from Gliclazide, Glibenclamide, Glisoxepide, Glipizide, Glimepiride, Gliquidone, Glyclopyrimide, Tolazamide, Tolbutamide, Chlorpropamide, Acetohexamide or combinations thereof.

2. Method of improving the efficacy of sulphonylurea treatment of Type-2 diabetes mellitus in a subject receiving a sulphonylurea anti-diabetic therapy, comprising administering to said subject, a composition comprising inulin or a source thereof which contains inulin in an amount of from about 4 grams/day to about 35 grams/day, in addition to an effective amount of the sulfonylurea anti-diabetic therapy, wherein the sulphonylurea is selected from Gliclazide, Glibenclamide, Glisoxepide, Glipizide, Glimepiride, Gliquidone, Glyclopyrimide, Tolazamide, Tolbutamide, Chlorpropamide, Acetohexamide or combinations thereof.

3. Method of treating hyperglycemia comprising the administration to a subject requiring such treatment of a composition comprising inulin, or a source thereof which contains inulin, in an amount of from about 4 grams/day to about 35 grams/day, and administration of an effective amount of a sulphonylurea, wherein the inulin is administered in an amount and for a time sufficient to improve a reduction, regulation or normalization of blood glucose concentration compared to treatment with said same sulphonylurea without inulin, and wherein the sulphonylurea is selected from Gliclazide, Glibenclamide, Glisoxepide, Glipizide, Glimepiride, Gliquidone, Glyclopyrimide, Tolazamide, Tolbutamide, Chlorpropamide, Acetohexamide or combinations thereof.

4. Method of reducing the development of, or ameliorating, hypoglycaemia in a subject treated with a sulphonylurea, comprising the administration to a subject requiring such treatment of a composition comprising inulin or a source of inulin, in addition to an effective amount of the sulfonylurea, the inulin or source of inulin being in an amount of from about 4 grams/day to about 35 grams/day and in an amount and for a time sufficient to reduce or ameliorate hypoglycemia, and wherein the sulphonylurea is selected from Gliclazide, Glibenclamide, Glisoxepide, Glipizide, Glimepiride, Gliquidone, Glyclopyrimide, Tolazamide, Tolbutamide, Chlorpropamide, Acetohexamide or combinations thereof.

5. A method of any one of claim 1, 2, 3 or 4, wherein inulin, or a source thereof which contains inulin, is administered simultaneously, either separately or together in the same composition, or sequentially, in any order, with the sulphonylurea.

6. A method of any one of claim 1, 2, 3 or 4, wherein the inulin is purified or pure inulin, or the source of inulin is a plant or part thereof, wherein the plant or part thereof is optionally selected from onion, leek, garlic, artichoke, salsify, agave, chicory and chicory root.

7. A method of any one of claim 1, 2, 3 or 4, wherein inulin, or a source thereof which contains inulin, is administered in an amount of from about 10 grams/day to about 35 grams/day.

8. A method of any one of claim 1, 2, 3 or 4, wherein inulin, or a source thereof which contains inulin, is administered orally, optionally as a supplement in a food and/or a beverage.

9. A method of any one of claim 1, 2, 3 or 4, wherein inulin, or a source thereof which contains inulin, is administered in a pharmaceutical unit dosage form selected from a pill, tablet, caplet, tapsule and capsule, optionally where the pharmaceutical unit dosage form further comprises a sulphonylurea.

10. A method of any one of claim 1, 2, 3 or 4, wherein inulin is administered continuously for a period of about 2 months to about 6 months, or from about 4 months to about 6 months, or for as long as sulphonylurea is administered, or the inulin administration is continued after cessation of sulphonylurea administration.

* * * * *